(12) United States Patent
Kitahara et al.

(10) Patent No.: US 7,442,142 B2
(45) Date of Patent: Oct. 28, 2008

(54) AUTOMATIC TRANSMISSION

(75) Inventors: Tetsurou Kitahara, Shizuoka (JP); Kohei Tsuchiya, Shizuoka (JP)

(73) Assignee: JATCO Ltd, Shizuoka (JP)

( * ) Notice: Subject to any disclaimer, the term of this patent is extended or adjusted under 35 U.S.C. 154(b) by 277 days.

(21) Appl. No.: 11/493,601

(22) Filed: Jul. 27, 2006

(65) Prior Publication Data

US 2007/0066440 A1    Mar. 22, 2007

(30) Foreign Application Priority Data

Sep. 21, 2005    (JP) .............................. 2005-273011

(51) Int. Cl.
F16H 57/04    (2006.01)

(52) U.S. Cl. ..................................... 475/159

(58) Field of Classification Search ................ 475/159, 475/116, 146
See application file for complete search history.

(56) References Cited

U.S. PATENT DOCUMENTS 3,321,999 A * 5/1967 Greer .......................... 475/159
3,475,992 A * 11/1969 West, Jr. et al. ............. 475/146
4,903,548 A   2/1990 Hayakawa et al.
5,013,287 A   5/1991 Hayakawa et al.
2007/0298925 A1* 12/2007 Kitahara et al. ............. 475/159

FOREIGN PATENT DOCUMENTS

JP    2-042239 A    2/1990
JP    2-042240 A    2/1990

* cited by examiner

Primary Examiner—Sherry Estremsky
(74) Attorney, Agent, or Firm—Foley & Lardner LLP

(57) ABSTRACT

An automatic transmission includes a first brake including first clutch plates; a pump cover defining a first receiving chamber, and a second receiving chamber receiving a planetary gear; a first cylindrical portion including splines; a second cylindrical portion located radially inside the first cylindrical portion; a first cylinder chamber formed radially inside the first cylindrical portion; and a first piston including a first radially extending portion, and a second radially extending portion, the first piston being arranged to push the first clutch plates, by using the second radially extending portion, radially inside the first cylindrical portion. The automatic transmission further includes a lubricating oil supply hole located at a radial position which is between the first cylinder chamber and the first cylindrical portion, and which is separated from the first cylinder chamber in the radial direction; and a connection groove connecting the lubricating oil supply hole and the splines.

11 Claims, 5 Drawing Sheets

|     | B1 | C1 | C2 | C3 | B5 | B2 | B3 | B4 | F1  | F3  | F2  |
|-----|----|----|----|----|----|----|----|----|-----|-----|-----|
| 1st | O  |    |    | O  | O  | O  |    |    | (O) | (O) | (O) |
| 2nd |    |    |    | O  | O  | O  | O  |    |     | (O) | (O) |
| 3rd |    |    | O  |    | O  | O  | O  |    |     | (O) |     |
| 4th |    |    | O  | O  |    |    | O  |    |     |     |     |
| 5th |    | O  | O  | O  |    |    |    |    |     |     |     |
| 6th |    | O  |    | O  |    |    | O  |    |     |     |     |
| 7th | O  | O  |    | O  |    |    |    |    | (O) |     |     |
| Rev.| O  |    |    | O  |    |    |    | O  |     |     |     |

AUTOMATIC TRANSMISSION

BACKGROUND OF THE INVENTION

The present invention relates to an automatic transmission, and more especially to a structure for lubricating engagement elements of the automatic transmission.

Japanese Patent Application Publication Nos. H02 (1990)-42239 and H02 (1990)-42240 (corresponding to U.S. Pat. No. 4,903,548 and U.S. Pat. No. 5,013,287) show automatic transmissions including two multiple plate brakes disposed in a radial direction, and a pump cover integrally formed with cylinder chambers for pressing the multiple plate brakes.

SUMMARY OF THE INVENTION

However, the above-mentioned automatic transmission includes the two cylinder chambers disposed alongside each other in the radial direction, and accordingly it is necessary to extend a drain oil passage from an oil pump to an outer circumference of the pump cover. Therefore, the pump cover is increased in size, and size of the pump cover in the axial direction may be increased for ensuring clearance between the pump cover and a torque converter. Moreover, in this arrangement, the drain oil from the oil pump is only returned to an oil pan, and the drain oil is not used effectively.

It is an object of the present invention to provide an automatic transmission including a pair of cylinder chambers disposed alongside each other in a radial direction, and being devised to decrease in size, and to use an drain oil effectively.

According to one aspect of the present invention, an automatic transmission comprises: a first brake including first clutch plates, and selectively fixing a first rotating element of a planetary gear; a pump cover covering an oil pump, and defining a first receiving chamber receiving a torque converter, and a second receiving chamber receiving the planetary gear; a first cylindrical portion extending axially from the pump cover in the second receiving chamber, and including splines formed in an inner circumference of the first cylindrical portion, and arranged to support the first clutch plates of the first brake; a second cylindrical portion extending axially from the pump cover in the second receiving chamber, and being located radially inside the first cylindrical portion; a first cylinder chamber formed radially inside the first cylindrical portion, and arranged to generate a pressure for the first brake; a first piston including a first radially extending portion defining the first cylinder chamber with an outer circumference of the second cylindrical portion, and a second radially extending portion arranged to extend in a radial direction, and located radially outside the first cylinder chamber, the first piston being arranged to push the first clutch plates, by using the second radially extending portion, radially inside the first cylindrical portion; a lubricating oil supply hole located at a radial position which is between the first cylinder chamber and the first cylindrical portion, and which is separated from the first cylinder chamber in the radial direction, and arranged to supply the lubricating oil from the pump cover to the second receiving chamber in the axial direction; and a connection groove connecting the lubricating oil supply hole and the splines of the first radially extending portion.

DETAILED DESCRIPTION OF THE INVENTION

Figures 1, 2:
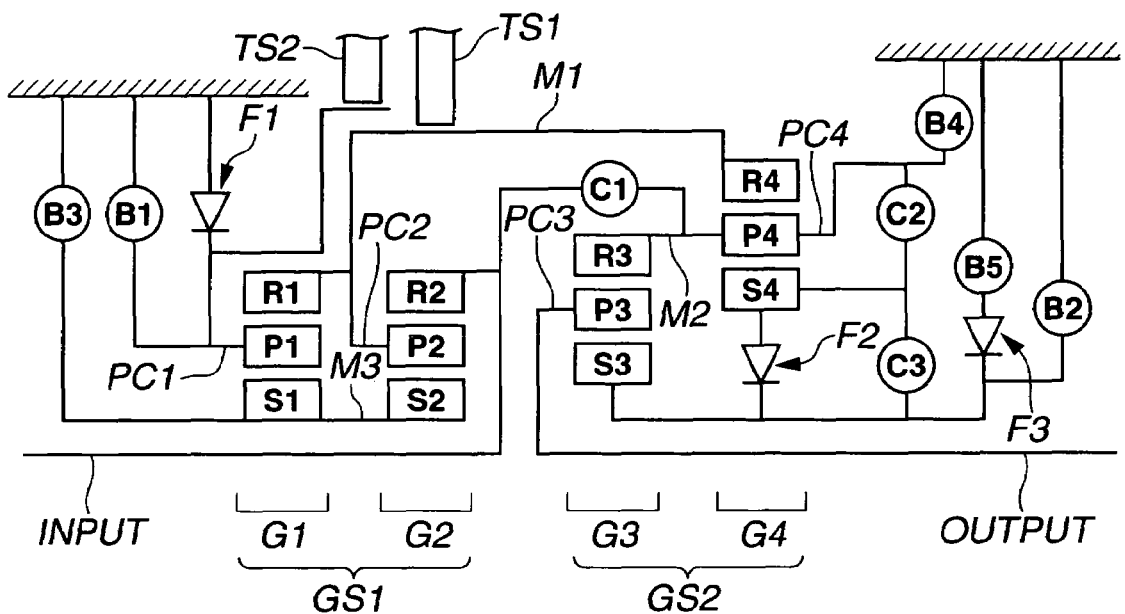
FIG. 1 is a skeleton diagram showing an automatic transmission for front engine rear wheel drive, arranged to attain seven forward speeds and one reverse speed, according to an embodiment of the present invention.
FIG. 2 is a table showing an engagement logic of friction engagement elements to select one of gear speeds of the automatic transmission of FIG. 1.

FIG. 1 shows an automatic transmission for an FR (Front engine Rear wheel drive) layout, arranged to attain seven forward speeds and one reverse speed. The automatic transmission includes an input shaft INPUT, an output shaft OUTPUT, a first planetary gear set GS1 (a first planetary gear G1 and a second planetary gear G2), and a second planetary gear set GS2 (a third planetary gear G3 and a fourth planetary gear G4). First planetary gear set GS1 is located on the input shaft's side (left side as shown in FIG. 1), and second planetary gear set GS2 is located on the output shaft's side (right side as shown in FIG. 1). In first planetary gear set GS1, first planetary gear G1 is located on the input shaft's side, and second planetary gear G2 is located on the output shaft's side. In second planetary gear set GS2, third planetary gear G3 is located on the input shaft's side, and fourth planetary gear G4 is located on the output shaft's side. The automatic transmission includes a first clutch C1, a second clutch C2, a third clutch C3, a brake B1, a second brake B2, a brake B3, and a fourth brake B4 serving as friction engagement elements. The automatic transmission includes a first one-way clutch F1, a second one-way clutch F2, and a third one-way clutch F3.

First planetary gear G1 is a single pinion type planetary gear including a first sun gear S1, a first ring gear R1, and a first career PC1 supporting first pinions P1 engaging with both first sun gear S1 and first ring gear R1.

Second planetary gear G2 is a single pinion type planetary gear including a second sun gear S2, a second ring gear R2, and a second career PC2 supporting second pinions P2 engaging with both second sun gear S2 and second ring gear R2.

Third planetary gear G3 is a single pinion type planetary gear including a third sun gear S3, a third ring gear R3, and a third career PC3 supporting third pinions P3 engaging with both third sun gear S3 and third ring gear R3.

Fourth planetary gear G4 is a single pinion type planetary gear including a fourth sun gear S4, a fourth ring gear R4, and a fourth career PC4 supporting fourth pinions P4 engaging with both fourth sun gear S4 and fourth ring gear R4.

Input shaft INPUT is connected with second ring gear R2 to transmit driving force from an engine (not shown) serving as a driving source through a torque converter and so on.

Output shaft OUTPUT is connected with third carrier PC3 to transmit output driving force through a final gear (not shown) to driving wheels of a vehicle.

A first connection member M1 connects first ring gear R1, second career PC2, and fourth ring gear R4 integrally.

A second connection member M2 connects third ring gear R3 and fourth career PC4 integrally.

A third connection member M3 connects first sun gear S1 and second sun gear S2 integrally.

First planetary gear G1 and second planetary gear G2 of first planetary gear set GS1 are connected by first connection member M1 and third connection member M3. Third planetary gear G3 and fourth planetary gear G4 of second planetary gear set GS2 are connected by second connection member M2.

First planetary gear set GS1 includes an input path for the torque inputted from input shaft INPUT to second ring gear R2. The torque inputted to first planetary gear set GS1 is outputted through first connection member M1 to second planetary gear set GS2.

Second planetary gear set GS2 includes an input path for the torque inputted from input shaft INPUT to second connection member M2, and an input path for the torque inputted from first connection member M1 to fourth ring gear R4. The torque inputted to second planetary gear set GS2 is outputted through third career PC3 to output shaft OUTPUT. When third clutch C3 is released and a rotational speed of fourth sun gear 54 is greater than a rotational speed of third sun gear S3, third sun gear S3 and fourth sun gear 54 rotate, respectively, at different speeds. In this state, third planetary gear G3 is connected through second connection member M2 to fourth planetary gear G4. Each of planetary gear G3 and fourth planetary gear G4 attains independent gear ratio (transmission ratio).

First clutch C1 selectively connects and disconnects input shaft INPUT with second connection member M2. Second clutch C2 selectively connects and disconnects fourth sun gear S4 with fourth career PC4. Third clutch C3 selectively connects and disconnects third sun gear S3 with fourth sun gear 54. Second one-way clutch F2 is disposed between third sun gear S3 and fourth sun gear S4.

Brake B1 (a second brake in the automatic transmission) selectively stops rotation of first career PC1. Second brake B2 selectively stops rotation of third sun gear S3. Brake B3 (a first brake in the automatic transmission) selectively stops rotation of third connection member M3 (first sun gear S1 and second sun gear S2 in the automatic transmission). Fourth brake B4 selectively stops rotation of fourth career PC4. Fifth brake B5 selectively stops rotation of third sun gear S3. Fifth brake B5 is disposed in series with third one-way clutch F3, and disposed in parallel with second brake B2.

Each of clutches C1, C2, and C3 and brakes B1, B2, B3, B4, and B5 is connected with a hydraulically-operated shift control apparatus (not shown) to produce engagement pressure (shown by solid line circles) and disengagement pressure (unmarked) in each gear speed of seven forward speeds and one reverse speed, as shown in FIG. 2. As the shift control apparatus, it is possible to employ an electrically-controlled type, a hydraulically-controlled type, and an electrically and hydraulically controlled type.

Figure 3:
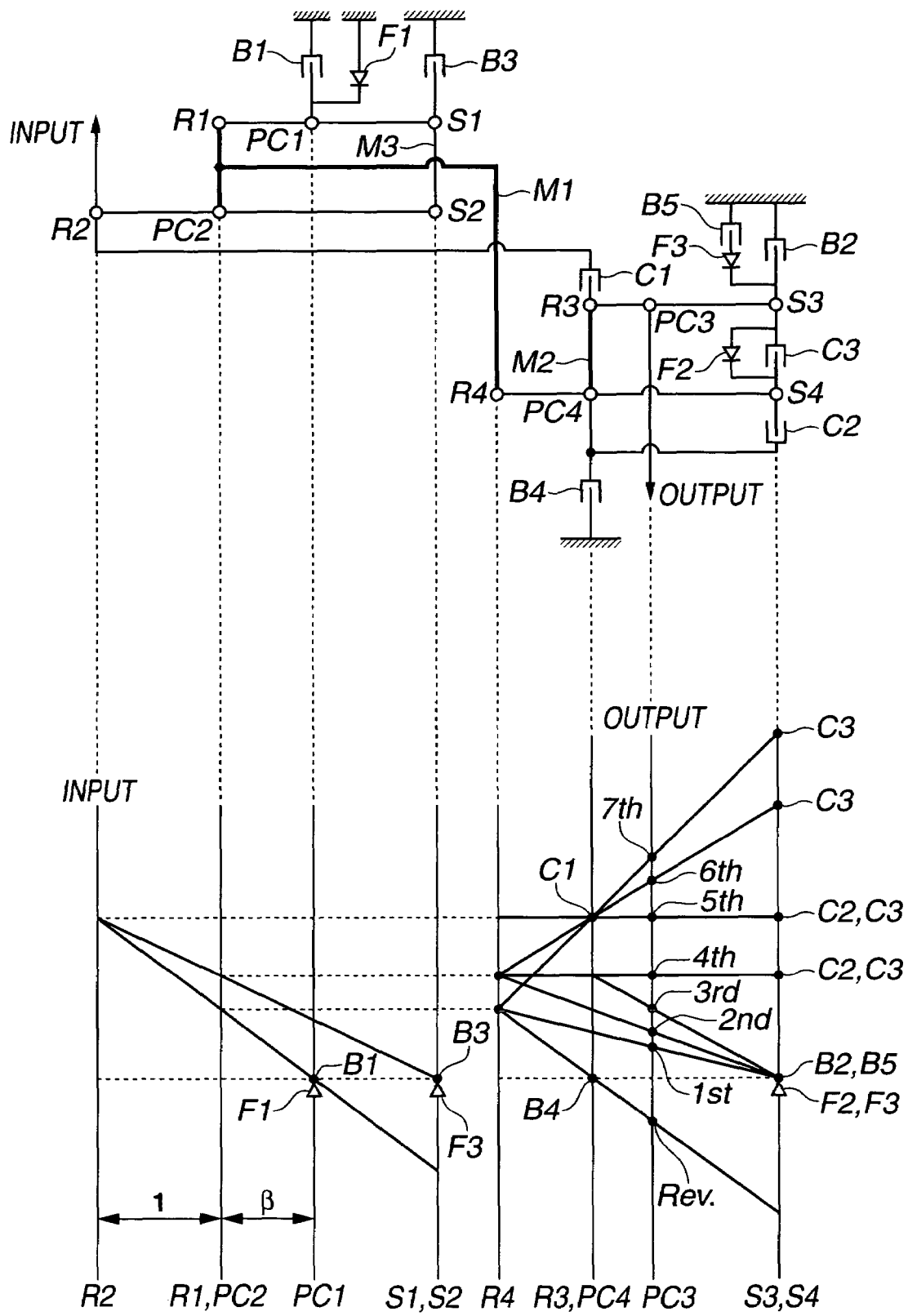
FIG. 3 is a speed diagram showing rotation state or stop state of each member in each gear speed of seven forward speeds and one reverse speed.

FIG. 2 shows a clutch schedule of the automatic transmission to attain the seven forward speeds and one reverse speed. FIG. 3 shows a speed diagram in each gear speed of the automatic transmission.

[First speed] The first speed is attained by the engagement of brake B1, the engagement of second brake B2, the engagement of fifth brake B5, and the engagement of third clutch C3, as shown in FIG. 2. Moreover, first one-way clutch F1 disposed in parallel with brake B1, third one-way clutch F3 disposed in series with fifth brake B5, and second one-way clutch F2 disposed in parallel with third clutch C3 also act for transmitting the torque.

In the first speed, the rotation is inputted from input shaft INPUT to second ring gear R2, and the rotational speed is reduced by first planetary gear set GS1 for the engagement of brake B1. This rotation from first planetary gear set GS1 is outputted through first connection member M1 to fourth ring gear R4, and the rotational speed is reduced by second planetary gear set GS2 for the engagement of second brake B2 and third clutch C3. This rotation slowed down by second planetary gear set GS2 is outputted from third career PC3.

As shown in the speed diagram of FIG. 3, the first speed is defined (determined) by a line connecting an engagement point of brake B1 arranged to decelerate the output rotation of the engine and an engagement point of second brake B2 arranged to decelerate the decelerated rotation from first planetary gear set GS1. The rotation inputted from input shaft INPUT is slowed down, and outputted from output gear OUTPUT.

In the first speed, the torque is transmitted through brake B1, second brake B2 (fifth brake B5 and third one-way clutch F3), third clutch C3, first connection member M1, second connection member M2, and third connection member M3. That is, first planetary gear set GS1 and second planetary gear set GS2 act for transmitting the torque.

[Second speed] The second speed is achieved by the engagement of second brake B2, the engagement of brake B3, the engagement of fifth brake B5, and the engagement of third clutch C3, as shown in FIG. 2. Moreover, third one-way clutch F3 disposed in series with fifth brake B5, and second one-way clutch F2 disposed in parallel with third clutch C3 also act for transmitting the torque.

In the second speed, the rotation is inputted from input shaft INPUT to second ring gear R2, and the rotational speed is reduced only by second planetary gear G2 for the engagement of brake B3. This rotation from second planetary gear G2 is outputted through first connection member M1 to fourth ring gear R4, and the rotational speed is reduced by second planetary gear set GS2 for the engagement of second brake B2 and third clutch C3. This rotation slowed down by second planetary gear set GS2 is outputted from third career PC3.

As shown in the speed diagram of FIG. 3, the second speed is determined by a line connecting an engagement point of brake B3 arranged to decelerate the output rotation of the engine and the engagement point of second brake B2 arranged to decelerate the decelerated rotation from second planetary gear G2. The rotation inputted from input shaft INPUT is slowed down, and outputted from output gear OUTPUT.

In the second speed, the torque is transmitted through brake B3, second brake B2 (fifth brake B5 and third one-way clutch F3), third clutch C3, first connection member M1, second connection member M2, and third connection member M3. That is, second planetary gear G2 and second planetary gear set GS2 act for transmitting the torque.

In the case of upshift from the first speed to the second speed, brake B1 is released early, and brake B3 starts the engagement. Subsequently, first one-way clutch F1 is released when engagement capacity (torque capacity) of brake B3 is ensured. Accordingly, it is possible to improve accuracy of shift timing.

[Third speed] The third speed is achieved by the engagement of brake B3, the engagement of second brake B2, the engagement of fifth brake B5, and the engagement of second clutch C2, as shown in FIG. 2. Moreover, third one-way clutch F3 disposed in series with fifth brake B5 is also used for transmitting the torque.

In the third speed, the rotation is inputted from input shaft INPUT to second ring gear R2, and the rotational speed is reduced by second planetary gear G2 for the engagement of brake B3. This rotation from second planetary gear G2 is outputted through first connection member M1 to fourth ring gear R4. Fourth planetary gear G4 rotates integrally for the engagement of second clutch C2. The rotation inputted from fourth career PC4 integrally rotating with fourth ring gear R4 is transmitted through second connection member M2 to third ring gear R3, and the rotational speed is reduced by third planetary gear G3 for the engagement of second brake B2. This rotation having the rotational speed reduced by third planetary gear G3 is outputted from third career PC3. In this way, fourth planetary gear G4 acts for the torque transmission, but does not function for reducing the rotational speed.

As shown in the speed diagram of FIG. 3, the third speed is defined by a line connecting the engagement point of brake B3 arranged to decelerate the output rotation of the engine and the engagement point of second brake B2 arranged to decelerate the decelerated rotation from second planetary gear G2. The rotation inputted from input shaft INPUT is decelerated, and outputted from output gear OUTPUT.

In the third speed, the torque is transmitted through brake B3, second brake B2 (fifth brake B5 and third one-way clutch F3), second clutch C2, first connection member M1, second connection member M2, and third connection member M3. That is, second planetary gear G2 and second planetary gear set GS2 act for transmitting the torque.

In the case of upshift from the second speed to the third speed, third clutch C3 is released early, and second clutch C2 starts to be engaged. Subsequently, second one-way clutch F2 is released when the engagement capacity (torque capacity) of second clutch C2 is ensured. Accordingly, it is possible to improve the accuracy of shift timing.

[Fourth speed] The fourth speed is achieved by the engagement of brake B3, the engagement of second clutch C2, and the engagement of third clutch C3, as shown in FIG. 2.

In the fourth speed, the rotation is inputted from input shaft INPUT to second ring gear R2, and the rotational speed is reduced only by second planetary gear G2 for the engagement of brake B3. This rotation from second planetary gear G2 is outputted through first connection member M1 to fourth ring gear R4. Second planetary gear set GS2 rotates integrally for the engagement of second clutch C2 and third clutch C3. The rotation inputted to forth ring gear R4 is directly (entirely) outputted from third career PC3.

As shown in the speed diagram of FIG. 3, the fourth speed is defined by a line connecting the engagement point of brake B3 arranged to decelerate the output rotation of the engine and an engagement point of second clutch C2 and third clutch C3 arranged to directly output the decelerated rotation from second planetary gear G2. The rotation inputted from input shaft INPUT is decelerated, and outputted from output gear OUTPUT.

In the fourth speed, the torque is transmitted through brake B3, second clutch C2, third clutch C3, first connection member M1, second connection member M2, and third connection member M3. That is, second planetary gear G2 and second planetary gear set GS2 act for transmitting the torque.

In the case of upshift from the third speed to the fourth speed, second brake B2 is released early, and third clutch C3 starts the engagement. Subsequently, third one-way clutch F3 is released when the engagement capacity (torque capacity) of third clutch C3 is ensured. Accordingly, it is possible to improve the accuracy of shift timing.

[Fifth speed] The fifth speed is achieved by the engagement of first clutch C1, the engagement of second clutch C2, and the engagement of third clutch C3, as shown in FIG. 2.

In the fifth speed, the rotation of input shaft INPUT is transmitted to second connection member M2 for the engagement of first clutch C1. Third planetary gear G3 rotates integrally for the engagement of second clutch C2 and third clutch C3. Accordingly, the rotation imputed from input shaft INPUT is directly (entirely) outputted from third career PC3.

As shown in the speed diagram of FIG. 3, the fifth speed is defined by a line connecting an engagement point of first clutch C1 arranged to directly output the output rotation from the engine and the engagement point of second clutch C2 and third clutch C3. The rotation inputted to input shaft INPUT is directly outputted from output gear OUTPUT.

In the fifth speed, the torque is transmitted through first clutch C1, second clutch C2, third clutch C3, and second connection member M2. That is, the torque is transmitted only by third planetary gear G3.

[Sixth speed] The sixth speed is achieved by the engagement of first clutch C1, the engagement of third clutch C3, and the engagement of brake B3, as shown in FIG. 2.

In the sixth speed, the rotation of input shaft INPUT is inputted to second ring gear R2 and second connection member M2 for the engagement of first clutch C1. The rotation decelerated by second planetary gear G2 for the engagement of brake B3 is outputted through first connection member M1 to fourth ring gear R4. For the engagement of third clutch C3, second planetary gear set GS2 outputs, from third career PC3, rotation determined by the rotation of fourth ring gear R4 and the rotation of second connection member M2.

As shown in the speed diagram of FIG. 3, the sixth speed is defined by a line connecting the engagement point of brake B3 arranged to reduce the output rotation of the engine by second planetary gear G2, the engagement point of first clutch C1 arranged to directly transmit the output rotation of the engine to second connection member M2, and the engagement point of third clutch C3 of second planetary gear set GS2. The rotation inputted to input shaft INPUT is accelerated, and outputted from output gear OUTPUT.

In the sixth speed, the torque is transmitted through first clutch C1, third clutch C3, brake B3, first connection member M1, second connection member M2, and third connection member M3. That is, second planetary gear G2 and second planetary gear set GS2 act for transmitting the torque.

[Seventh speed] The seventh speed is achieved by the engagement of first clutch C1, the engagement of third clutch C3, and the engagement of brake B1 (first one-way clutch F1), as shown in FIG. 2.

In the seventh speed, the rotation of input shaft INPUT is inputted to second ring gear R2 and second connection member M2 for the engagement of first clutch C1. The rotation reduced by first planetary gear set GS1 for the engagement of brake B1 is outputted through first connection member M1 to fourth ring gear R4. For the engagement of third clutch C3, second planetary gear set GS2 outputs, from third career PC3, rotation defined by the rotation of fourth ring gear R4 and the rotation of second connection member M2.

As shown in the speed diagram of FIG. 3, the seventh speed is defined by a line connecting the engagement point of brake B1 arranged to decelerate the output rotation of the engine by first planetary gear set GS1, the engagement point of first clutch C1 arranged to directly transmit the output rotation of the engine to second connection member M2, and the engagement point of third clutch C3 of second planetary gear set GS2. The rotation inputted to input shaft INPUT is accelerated, and outputted from output gear OUTPUT.

In the seventh speed, the torque is transmitted through first clutch C1, third clutch C3, brake B1, first connection member M1, second connection member M2, and third connection member M3. That is, first planetary gear set GS1 and second planetary gear set GS2 act for transmitting the torque.

[Reverse speed] The reverse speed is achieved by the engagement of third clutch C3, the engagement of brake B1, and the engagement of fourth brake B4, as shown in FIG. 2.

In the case of the reverse speed, the rotation is decelerated by first planetary gear set GS1 for the engagement of brake B1, and outputted through first connection member M1 to fourth ring gear R4. For the engagement of third clutch C3 and fourth brake B4, second planetary gear set GS2 outputs, from third career PC3, rotation defined by the rotation of fourth ring gear R4 and the fixation of second connection member M2.

As shown in the speed diagram of FIG. 3, the reverse speed is defined by a line connecting an engagement point of brake B1 arranged to decelerate the output rotation of the engine by first planetary gear set GS1, an engagement point of fourth brake B4 arranged to fix the rotation of second connection member M2, and the engagement point of third clutch C3 of second planetary gear set GS2. The rotation inputted to input shaft INPUT is reversed and decelerated, and outputted from output gear OUTPUT.

In the reverse speed, the torque is transmitted through third clutch C3, brake B1, fourth brake B4, first connection member M1, second connection member M2, and third connection member M3. That is, first planetary gear set GS1 and second planetary gear set GS2 act for transmitting the torque.

Figure 4:
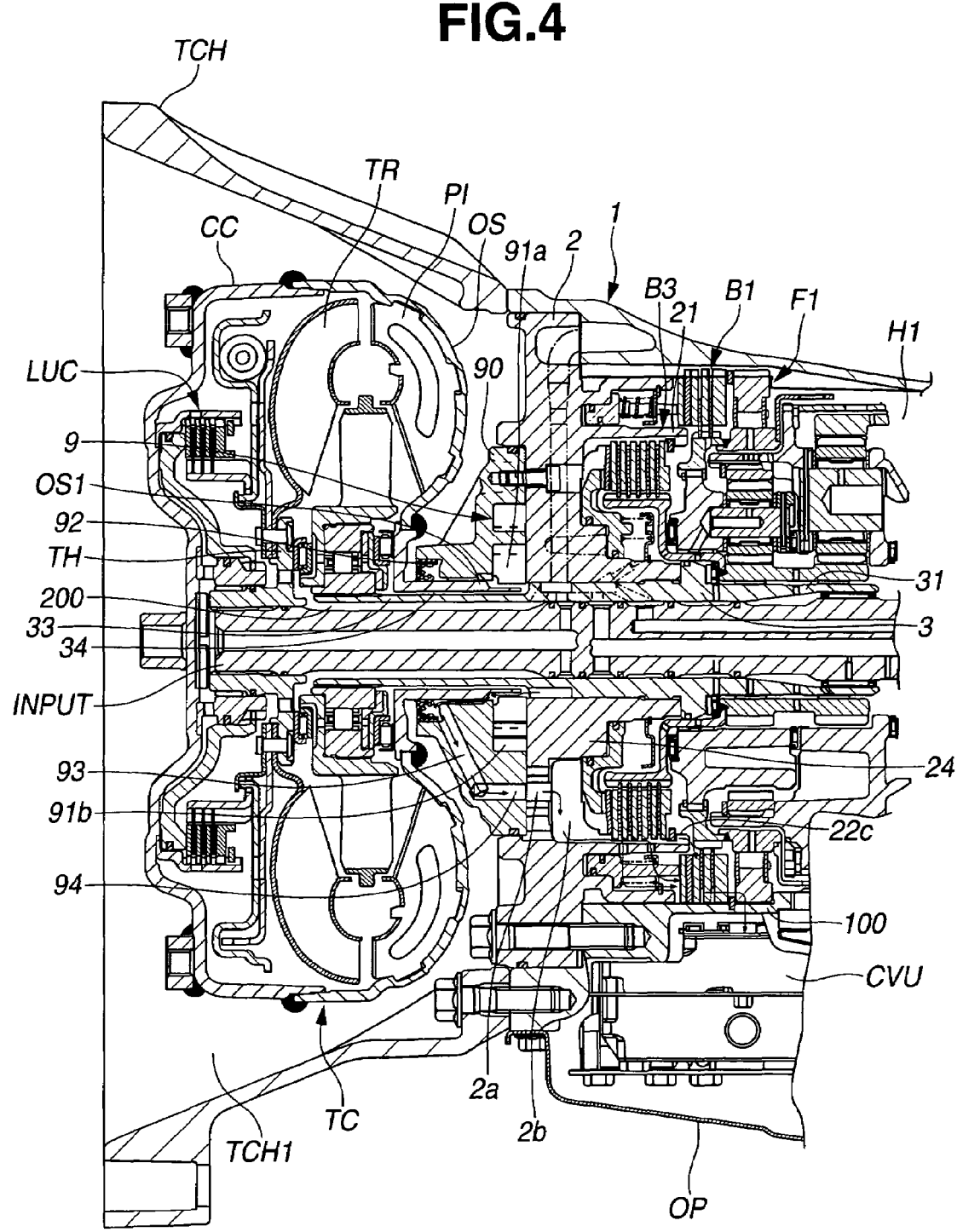
FIG. 4 is a sectional view showing a torque converter and a first planetary gear of the automatic transmission of FIG. 1.
Figure 5:
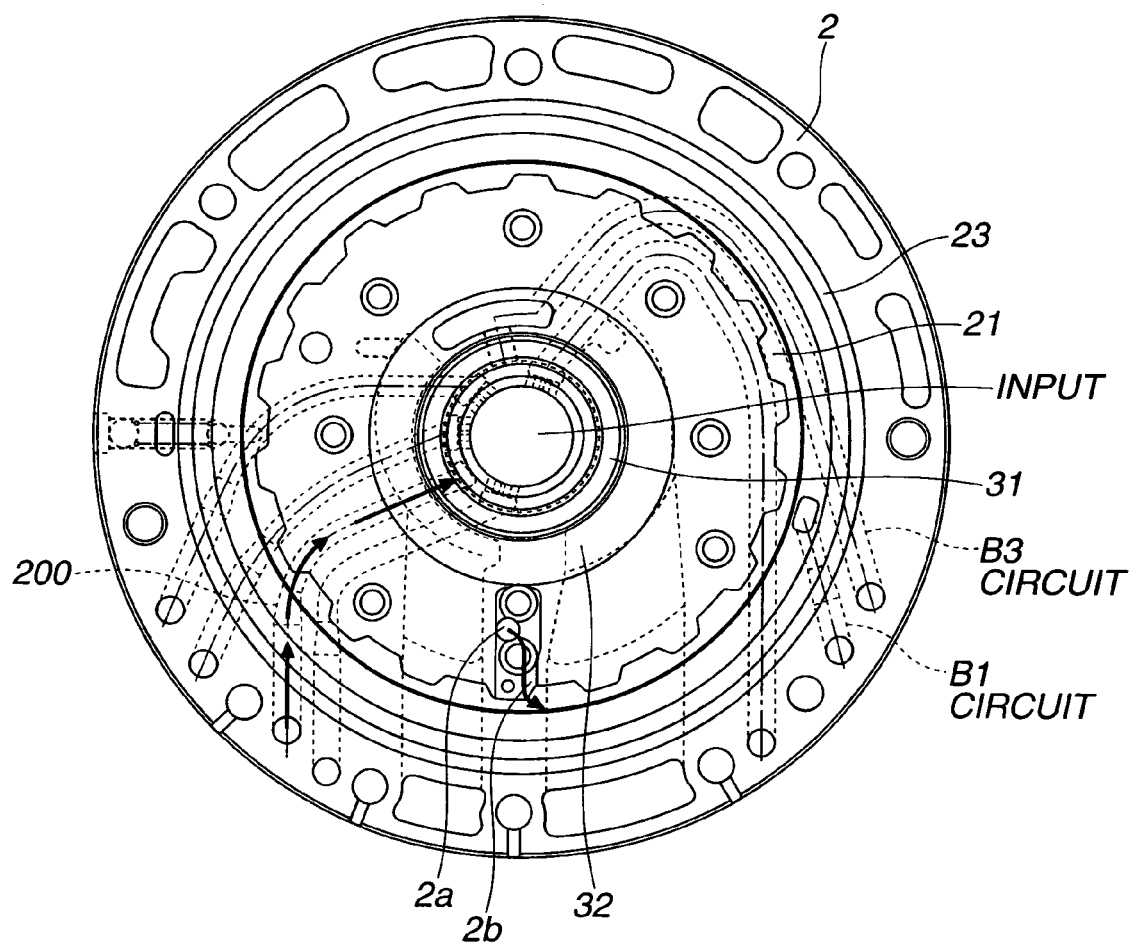
FIG. 5 is a front view showing a pump cover of the automatic transmission of FIG. 1.

FIG. 4 shows an arrangement designed in accordance with the skeleton diagram and layout of FIG. 1, and shows, in section, portion near a torque converter TC and first planetary gear G1. FIG. 5 shows a front view of pump cover 2.

A torque converter housing TCH is formed with a first receiving chamber TCH1 for receiving torque converter TC. Torque converter TC includes a converter cover CC, an outer shell OS, a turbine runner TR, and a lockup clutch LUC. Converter cover CC is directly connected with the engine. Outer shell OS is connected with converter cover CC by welding. A pump impeller PI is connected with an inner circumference of outer shell OS by brazing. Turbine runner TR rotates by receiving oil flow from outer shell OS. Lockup clutch LUC is arranged to connect turbine runner TR and converter cover CC integrally.

Outer shell OS includes a driving claw OS1 extending axially toward pump cover 2 (rightward as viewed in FIG. 4), and engaging with an inner gear 91a of an oil pump 9. Turbine runner TR includes a turbine hub TH engaging with input shaft INPUT by splines. A stator shaft 3 is engaged with (fit in) an inner circumference of pump cover 2. Stator shaft 3 includes an extension portion 33 extending toward torque converter TC (leftward as viewed in FIG. 4), and supporting a stator of torque converter TC.

Oil pump 9 is a gear pump disposed between a pump hosing 90 and pump cover 2. Oil pump 9 generates hydraulic pressure by engagement of inner gear 91a and an outer gear 91b in a state in which a center of inner gear 91a is off a center of outer gear 91b. Pump housing 90 includes an oil seal 92, a lubricant passage 93, and an axial oil passage 94. Oil seal 92 liquid-tightly seals between driving claw OS1 and pump housing 90.

An oil passage 34 is formed in a radial interspace between driving claw OS1 and extension portion 33. Oil passage 34 is arranged to supply converter pressure into torque converter TC. Pump cover 2 is formed with an oil passage 200 arranged to supply oil passage 34 with the converter pressure regulated by a control valve unit CVU, as shown in the front view of pump cover 2 of FIG. 5.

Figure 6:
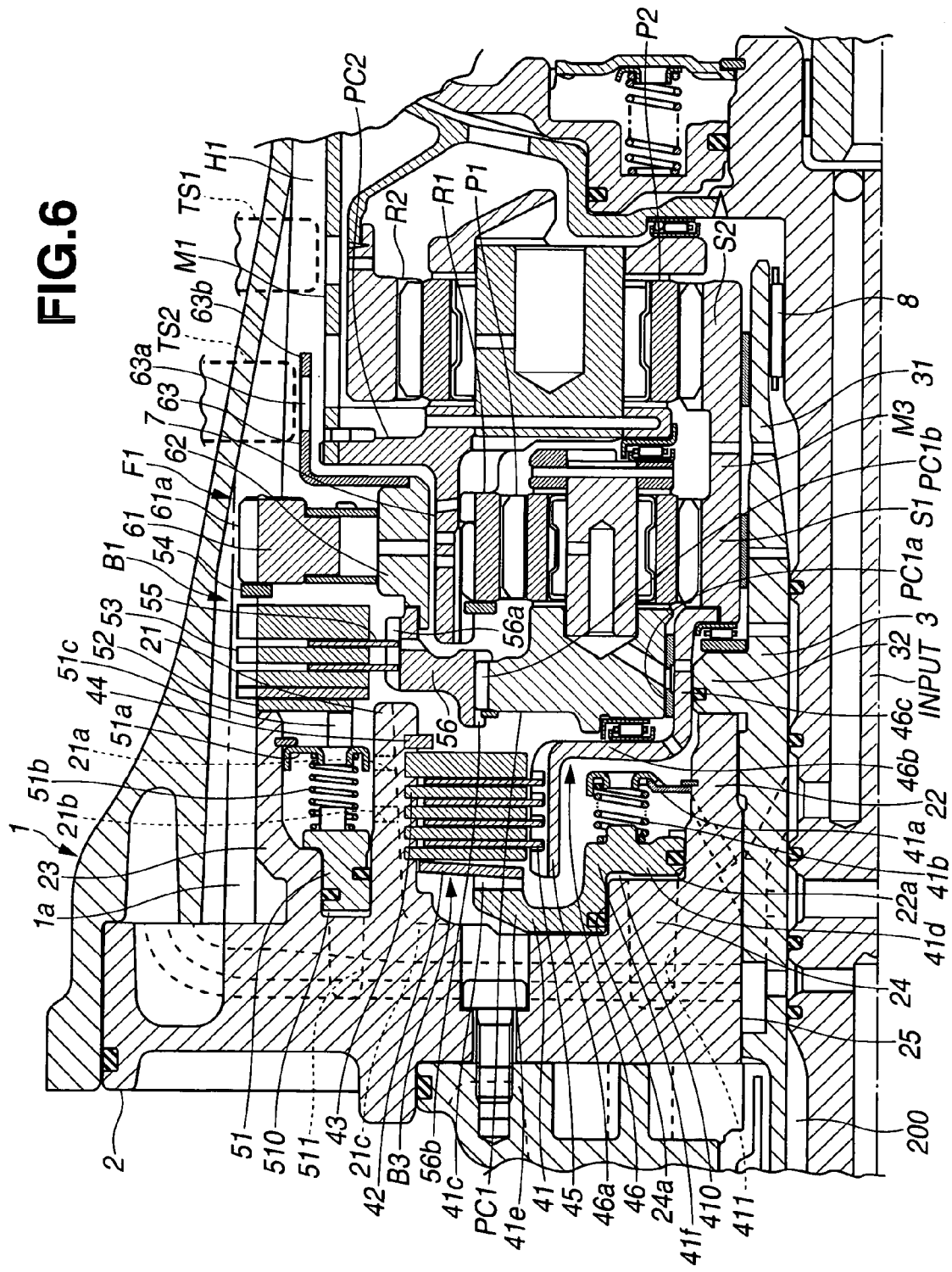
FIG. 6 is an enlarged sectional view showing an arrangement near of the first planetary gear of the automatic transmission of FIG. 1.

FIG. 6 shows a periphery of first planetary gear G1 in cross section. Splines 1a are formed on an opening of an end portion of transmission housing 1 located on the input shaft's side (left side as shown in FIG. 6). Splines 1a are engaged with second clutch plates 53 and an outer race 61 described later. Pump cover 2 is inserted and fixed to the opening of the end portion of the input side of transmission housing 1. Pump cover 2 defines first receiving chamber TCH1 for receiving torque converter TC, and a second receiving chamber H1 for receiving the planetary gears.

Pump cover 2 includes a first cylindrical portion (central cylindrical portion) 21 extending toward the output side (rightward as viewed in FIG. 6), a second cylindrical portion (inner cylindrical portion) 22 extending toward the output side (rightward in FIG. 6), and a third cylindrical portion (outer cylindrical portion) 23 extending toward the output side (rightward in FIG. 6). First cylindrical portion 21 extends in the axial direction. Second cylindrical portion 22 extends in the axial direction, radially inside first cylindrical portion 21. Third cylindrical portion 23 extends in the axial direction, radially outside first cylindrical portion 21. Second cylindrical portion 22 is provided with a stepped portion 24 which is formed on one part of an outer circumference of second cylindrical portion 22, and which is greater in diameter than second cylindrical portion 22. Stepped portion 24 extends axially from pump cover 2 in the form of cylinder. Stepped portion 24 raises radially from the outer circumference of second cylindrical portion 22. Stepped portion 24 includes a sliding portion 24a provided on an outer circumference of stepped portion 24, radially inside a second radial extension 41e described later, and arranged to slide in contact with an axial extension 41f. A support hole 25 is provided in an inner circumference of second cylindrical portion 22. A sliding portion 22a is provided on the outer circumference of second cylindrical portion 22, near stepped portion 24, and arranged to slide in contact with an inner circumference of a first radial extension 41d described later.

Third cylindrical portion 23 and first cylindrical portion 21 define a second cylinder chamber 510 receiving a second piston 51 of brake B1. A spring 51b and a spring retainer 51a for supporting spring 51b are provided radially inside third cylindrical portion 23. Spring 51b urges second piston 51 to the pump cover 2's side (the left side as viewed in FIG. 6).

Splines 21c are formed on an inner circumference of first cylindrical portion 21. First clutch plates 43 of brake B3 engage with spline 21c so as to slide in the axial direction. Clutch plates 45 engage with a third brake hub 46 described later. First clutch plates 43 and clutch plates 45 are arranged alternatively, and fixed by a snap ring 44 in the axial direction. A plate spring 42 is provided at one of first clutch plates 43 on the pump cover's side (the left side as shown in FIG. 6). Radial oil passages 21a and 21b are arranged radially alongside (beside) each other for conducting the lubricant oil radially outwards.

A first piston 41 of brake B3 is disposed radially inside first cylindrical portion 21, radially outside stepped portion 24 and second cylindrical portion 22. First piston 41 includes first radial extension or first radially extending portion 41d, second radial extension or second radially extending portion 41e, and axial extension or axially extending portion 41f. First piston 41 is in the form of crank or bent shape. First piston 41 is moved in the axial direction so that axially extending portion 41f is sealingly slid with sliding portion 24a formed on the outer circumference of stepped portion 24, and that the inner circumference of first radially extending portion 41d is sealingly slid with sliding portion 22a formed on the outer circumference of second cylindrical portion 22. Consequently, a first cylinder chamber 410 is defined by the outer circumference of second cylindrical portion 22, stepped portion 24, and first radially extending portion 41d and axially extending portion 41f of first piston 41. In general, the piston is received in a recessed portion in which the cylinder chamber is formed. However, the recessed portion serving as the cylinder chamber causes reduction in the strength. Contrarily, it is possible to ensure the strength of pump cover 2 because first cylinder chamber 410 is provided on the raised portion of stepped portion 24.

A spring 41b and a spring retainer 41a for supporting spring 41b are provided radially outside second cylindrical portion 22. Spring 41b urges first piston 41 to the pump cover 2's side (the left side in FIG. 6).

Support hole 25 is provided on the inner circumference of second cylindrical portion 22. Stator shaft 3 is inserted and fixed in support hole 25 by press fit. A radially extended portion or larger diameter portion 32 is provided on an outer circumference of stator shaft 3. Stator shaft 3 is positioned by contact of radially extended portion 32 and an axial end of second cylindrical portion 22. A sun gear support portion 31 is provided on the output shaft's side of larger diameter portion 32. Sun gear support portion 31 rotatably supports third rotation member M3 radially outside sun gear support portion 31. Input shaft INPUT is rotatably supported on the inner circumference of stator shaft 3. Needle bearings 8 are disposed between the inner circumference of sun gear support portion 31 and input shaft INPUT.

A lubricant oil supply hole 2a is formed radially outside stepped portion 24, radially inside first cylindrical portion 21. Lubricant oil supply hole 2a is formed in pump cover 2. Connection groove 2b is formed in pump cover 2 around lubricant oil supply hole 2a, as shown in FIG. 5. Connection groove 2b connects lubricant oil supply hole 2a and splines 21c formed on the inner circumference of first cylindrical portion 21.

First sun gear S1 of first planetary gear G1 is connected with third brake hub 46 arranged to fix the rotation of first sun gear S1 (third rotation member M3) to pump cover 2. Third brake hub 46 includes a spline portion 46a, a bottom portion 46b, and a support cylindrical portion 46c. Support cylindrical portion 46c is disposed between radially extended portion 32 and first career PC1 described later. Bottom portion 46b extends radially outwards from an axial end portion of support cylindrical portion 46c on the pump cover 2's side (the left side as shown in FIG. 6). Spline portion 46a extends from bottom portion 46b toward the input shaft's side (leftward as shown in FIG. 6).

First career PC1 of first planetary gear G1 includes a career support portion PC1a and a spline portion PC1b. Career support portion PC1a is slidably supported through a bush on the outer circumference of support cylindrical portion 46c. Spline portion PC1b is formed in the axial direction on an outer circumference of first career PC1. A first brake hub 56 is splined with spline portion PC1b. First brake hub 56 includes an inner spline portion 56b formed on an inner circumference of first brake hub 56, and an outer spline portion 56a formed on an outer circumference of first brake hub 56. Inner spline portion 56b is splined with spline portion PC1b. Outer spline portion 56a is spline with clutch plates 55. An inner race 62 of first one-way clutch F1 is integrally fixed with an axial end portion of first brake hub 56 on the output shaft's side (right side as shown in FIG. 6).

Splines are formed on an outer circumference of first ring gear R1 of first planetary gear G1. This splines are engaged with a connection member 7 extending axially from second pinion career PC2 toward the input shaft's side. Second pinion career PC2 is connected with first connection member M1 radially outside second planetary gear G2.

First one-way clutch F1 includes splines 61a engaged with splines 1a formed on the inner circumference of transmission housing 1, outer race 61 fixed by a snap ring 54 in the axial direction, inner race 62, and sprags disposed between outer race 61 and inner race 62. Transmission housing 1 is formed with a drain hole 100 located radially outside outer race 61. Drain hole 100 allows flow of the drain oil into an oil pan OP receiving control valve unit CVU.

A sensor member 63 for a second rotation sensor TS2 is fixed to an axial end portion of inner race 62 on the output shaft's side. Sensor member 63 includes an extending portion 63b extending in the axial direction to overlap first connection member M1 in the axial direction. Extending portion 63b is provided with a plurality of through holes 63a located at a regular interval in the circumferential direction. Second rotation sensor TS2 senses movement of through holes 63a by variation in magnetic field, and measures or determines the rotational speed of first career PC1.

[Lubricant path for lubricant oil] Control valve unit CVU regulates the converter pressure supplied into torque converter TC, and the converter pressure is supplied through oil passage 200 to a radially central portion, as shown in FIG. 5. This radially central portion is a portion at which inner gear 91a and driving claw OS1 are engaged. Most of the oil is supplied to oil passage 34, and part of the oil flows to an interspace or gap between driving claw OS1 and pump housing 90. The oil flowing through the interspace lubricates a sliding surface of oil seal 92, and is drained to lubricant passage 93. The oil drained to lubricant passage 93 is supplied through axial lubricant passage 94 to lubricant oil supply hole 2a of pump cover 2.

The lubricant oil drained from lubricant oil supply hole 2a flows through connection groove 2b to splines 21c. The lubricant oil supplied to splines 21c is supplied through radial oil passages 21a and 21b to second piston 51 of brake B1 disposed radially outside splines 21c. Moreover, the lubricant oil supplied to splines 21c lubricates first clutch plates 43 and clutch plates 45, and is supplied from the axial end portion of first cylindrical portion 21 on the first planetary gear's side (the right side in FIG. 6), to second clutch plates 53 and 55 of brake B1. The lubricating oil which has lubricated brake B1 is recirculated through drain hole 100 formed in transmission housing 1 to oil pan OP.

In the illustrated embodiment, the automatic transmission includes brake B3 (a first brake in the automatic transmission) including first clutch plates 43, and selectively fixing sun gear (a first rotating element in the automatic transmission) S1 of planetary gear G1; pump cover 2 covering oil pump 9, and defining first receiving chamber TCH1 receiving torque converter TC, and second receiving chamber H1 receiving the planetary gear G1; first cylindrical portion 21 extending axially from the pump cover 2 in the second receiving chamber H1, and including splines 21c formed in the inner circumference of the first cylindrical portion 21, and arranged to support the first clutch plates 43 of the brake (the first brake) B3; second cylindrical portion 22 extending axially from the pump cover 2 in the second receiving chamber H1, and being located radially inside the first cylindrical portion 21; first cylinder chamber 410 formed radially inside the first cylindrical portion 21, and arranged to generate the pressure for the first brake B3; first piston 41 including first radially extending portion 41d defining the first cylinder chamber 410 with the outer circumference of the second cylindrical portion 22, and second radially extending portion 41e arranged to extend in the radial direction, and located radially outside the first cylinder chamber 410, the first piston 41 being arranged to push the first clutch plates 43, by using the second radially extending portion 41e, radially inside the first cylindrical portion 21; lubricating oil supply hole 2a located at the radial position which is between the first cylinder chamber 410 and the first cylindrical portion 21, and which is separated from the first cylinder chamber 410 in the radial direction, and arranged to supply the lubricating oil from the pump cover 2 to the second receiving chamber H1 in the axial direction; and connection groove 2b connecting the lubricating oil supply hole 2a and the splines 21c of the first radially extending portion 21.

That is, the brake is disposed on pump cover 2 so that the clutch plates are off first cylinder chamber 410 in the radial direction, and that first clutch plate 43 are pushed by piston 41 radially inside first cylindrical portion 21. Accordingly, it is possible to ensure the interspace radially between spline 21c and first piston 41. In this case, lubricating oil supply opening 2a is formed between first cylinder chamber 410 and first cylindrical portion 21, and it is possible to supply the lubricating oil to first clutch plate 43. Moreover, it is possible to supply the lubricating oil along splines 21c efficiently because of the provision of connection groove 2b.

The automatic transmission according to the embodiment includes brake (a second brake in the automatic transmission) B1 selectively fixing first career PC1 (a second rotation member in the automatic transmission). Brake (the second brake) B1 includes second clutch plates 53 located radially outside first cylindrical portion 21, axially between the planetary gear and the axial end portion of first cylindrical portion 21 which confronts the planetary gear.

Accordingly, it is possible to efficiently supply the lubricant oil which has lubricated splines 21c, to second clutch plates 53 from the radial inside. Radial oil passages 21a and 21b are formed in first cylindrical portion 21, and accordingly, it is also possible to supply the lubricant oil to second clutch plates 53 and clutch plates 55 from the axial direction, and thereby to improve lubrication efficiency.

The automatic transmission according to the embodiment includes the third cylindrical portion 23 extending axially from the pump cover 2 in the second receiving chamber H1, and being located radially outside the first cylindrical portion 21, and second cylinder chamber 510 formed between the first cylindrical portion 21 and the third cylindrical portion 23, and arranged to generate the pressure for the brake (the second brake) B1; and the pump cover 2 is formed with the first oil passage 411 arranged to supply the hydraulic pressure to the first cylinder chamber 410, and the second oil passage 511 arranged to supply the hydraulic pressure to the second cylinder chamber 510.

Pump cover 2 serves as a vertical wall within transmission housing 1. Pump cover 2 can readily connect control valve unit CVU provided on the lower portion of transmission housing 1, to portions arranged to receive the hydraulic pressure supply, and located in the radial direction. Accordingly, it is possible to handle the lubricant passages readily, and to ensure the readiness of the manufacture because the passages for the supply of hydraulic pressure to first cylinder chamber 410 and second cylinder chamber 510 are formed only in pump cover 2.

In the illustrated embodiment, the pump cover 2 is formed with the torque converter pressure supply passage arranged to supply the hydraulic pressure from the radially central portion into the torque converter TC; the automatic transmission further comprises the pump housing 90 receiving the oil pump 9; and the pump housing 90 is formed with lubricating passages 93, 94 connecting the torque converter pressure supply passage and the lubricating oil supply hole 2a.

Pump cover 2 can readily connect control valve unit CVU and the portion arranged to receive the hydraulic pressure supply, and located in the radial position, as mentioned above. Therefore, pump cover 2 is formed with a plurality of oil passages, as shown in FIG. 5. Accordingly, it is difficult to further form the oil passages for lubrication in pump cover 2. In this case, lubricating oil passages 93 and 94 are formed in pump housing 90, and accordingly it is possible to readily supply the lubricating oil by using the leakage of the converter pressure. That is, there is no need to supply additional oil pressure for the lubrication from control valve unit CVU, and it is possible to simplify the structure.

Second cylindrical portion 22 includes stepped portion 24 radially extending in the axial direction on the first receiving chamber TCH1's side. First piston 41 includes axially extending portion 41f extending axially from the first end connected with the outer circumference of the first radially extending portion 41d, to the second end connected with the inner circumference of the second radially extending portion 41e, toward the first receiving chamber TCH1. First cylinder chamber 410 is defined by sliding portion 22a between the inner circumference of first radial extension 41d and the outer circumference of second cylindrical portion 22, and sliding portion 24a between the inner circumference of second radial extension portion 41e and the outer circumference of stepped portion 24.

In general, the cylinder chamber is formed in the recessed portion, the strength may be decreased for the deficiency of the thickness of the recessed portion. Moreover, if the recessed portion is formed to ensure thickness, the size in the axial direction is increased. Especially, input shaft INPUT is supported through stator shaft 3 at the radial center of pump cover 2, and therefore the strength is needed at the radial center of pump cover 2. Contrarily, in the illustrated embodiments, first piston 41 is disposed to cover stepped portion 24 of the raised portion, and it is possible to dispose first cylinder 410 without generating the reduction in the strength.

This application is based on a prior Japanese Patent Application No. 2005-273011. The entire contents of the Japanese Patent Application No. 2005-273011 with a filing date of Sep. 21, 2005 are hereby incorporated by reference.

Although the invention has been described above by reference to certain embodiments of the invention, the invention is not limited to the embodiments described above. Modifications and variations of the embodiments described above will occur to those skilled in the art in light of the above teachings. The scope of the invention is defined with reference to the following claims.

What is claimed is:

1. An automatic transmission comprising:
   a first brake including first clutch plates, and selectively fixing a first rotating element of a planetary gear;
   a pump cover covering an oil pump, and defining a first receiving chamber receiving a torque converter, and a second receiving chamber receiving the planetary gear;
   a first cylindrical portion extending axially from the pump cover in the second receiving chamber, and including splines formed in an inner circumference of the first cylindrical portion, and arranged to support the first clutch plates of the first brake;
   a second cylindrical portion extending axially from the pump cover in the second receiving chamber, and being located radially inside the first cylindrical portion;
   a first cylinder chamber formed radially inside the first cylindrical portion, and arranged to generate a pressure for the first brake;
   a first piston including a first radially extending portion defining the first cylinder chamber with an outer circumference of the second cylindrical portion, and a second radially extending portion arranged to extend in a radial direction, and located radially outside the first cylinder chamber, the first piston being arranged to push the first clutch plates, by using the second radially extending portion, radially inside the first cylindrical portion;

a lubricating oil supply hole located at a radial position which is between the first cylinder chamber and the first cylindrical portion, and which is separated from the first cylinder chamber in the radial direction, and arranged to supply the lubricating oil from the pump cover to the second receiving chamber in the axial direction; and a connection groove connecting the lubricating oil supply hole and the splines of the first cylindrical portion.

2. The automatic transmission as claimed in claim 1, wherein the pump cover is formed with the lubricating oil supply hole and the connection groove.

3. The automatic transmission as claimed in claim 1, wherein the automatic transmission further comprises a second brake selectively fixing a second rotating element of the planetary gear; and the second brake includes second clutch plates located radially outside the first cylindrical portion, axially between the planetary gear and an axial end portion of the first cylindrical portion which confronts the planetary gear.

4. The automatic transmission as claimed in claim 3, wherein the automatic transmission further comprises a third cylindrical portion extending axially from the pump cover in the second receiving chamber, and being located radially outside the first cylindrical portion, and a second cylinder chamber formed between the first cylindrical portion and the third cylindrical portion, and arranged to generate a pressure for the second brake; and the pump cover is formed with a first oil passage arranged to supply the hydraulic pressure to the first cylinder chamber, and a second oil passage arranged to supply the hydraulic pressure to the second cylinder chamber.

5. The automatic transmission as claimed in claim 1, wherein the automatic transmission further comprises a pump housing receiving the oil pump, and a torque converter pressure supply passage arranged to supply hydraulic pressure into the torque converter; and the pump housing is formed with a lubricating passage connecting the torque converter pressure supply passage and the lubricating oil supply hole.

6. The automatic transmission as claimed in claim 5, wherein the automatic transmission further comprises a stator shaft fit in an inner circumference of the pump cover; the torque converter includes an outer shell including a driving claw extending toward the pump cover; and the torque converter pressure supply passage is a gap between the stator shaft and the driving claw of the outer shell.

7. The automatic transmission as claimed in claim 6, wherein the oil pump includes an inner gear and an outer gear engaging with the inner gear so that the oil pump(9) generates the hydraulic pressure; and the driving claw of the outer shell is engaged with the inner gear.

8. The automatic transmission as claimed in claim 1, wherein the second cylindrical portion extends from a first end portion to a second end portion connected with the pump cover, and the second cylindrical portion includes a stepped portion located on the second end portion of the second cylindrical portion in the axial direction, and arranged to have an outside diameter larger than an outside diameter of the second cylindrical portion.

9. The automatic transmission as claimed in claim 8, wherein the first piston includes an axially extending portion extending axially from a first end connected with an outer circumference of the first radially extending portion, to a second end connected with an inner circumference of the second radially extending portion, toward the first receiving chamber.

10. The automatic transmission as claimed in claim 9, wherein the first piston is moved in the axial direction so that the axially extending portion is sealingly slid with a sliding portion formed on the outer circumference of the stepped portion, and that the inner circumference of first radially extending portion is sealingly slid with a sliding portion formed on the outer circumference of the second cylindrical portion.

11. The automatic transmission as claimed in claim 1, wherein the first cylindrical portion is formed with a radial oil passage extending in the radial direction.

* * * * *